(12) United States Patent
Petzoldt et al.

(10) Patent No.: US 7,211,691 B2
(45) Date of Patent: *May 1, 2007

(54) HETEROGENEOUSLY CATALYZED PARTIAL GAS PHASE OXIDATION OF PROPENE TO ACROLEIN

(75) Inventors: Jochen Petzoldt, Mannheim (DE); Martin Dieterle, Mannheim (DE); Heiko Arnold, Nanjing (CN); Wilhelm Ruppel, Mannheim (DE); Klaus-Joachim Mueller-Engel, Stutensee (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 516 days.

This patent is subject to a terminal disclaimer.

(21) Appl. No.: 10/784,825

(22) Filed: Feb. 24, 2004

(65) Prior Publication Data
US 2004/0192964 A1    Sep. 30, 2004

Related U.S. Application Data

(60) Provisional application No. 60/475,795, filed on Jun. 5, 2003.

(30) Foreign Application Priority Data
Mar. 25, 2003  (DE) ................ 103 13 210

(51) Int. Cl.
*C07C 51/16* (2006.01)
(52) U.S. Cl. ..................... 562/534; 562/545
(58) Field of Classification Search ........... 562/534, 562/545
See application file for complete search history.

(56) References Cited

U.S. PATENT DOCUMENTS

| 2004/0192963 A1 | 9/2004 | Dieterle et al. |
|---|---|---|
| 2004/0192964 A1 | 9/2004 | Petzoldt et al. |
| 2004/0192965 A1 | 9/2004 | Petzoldt et al. |
| 2004/0225158 A1 | 11/2004 | Dieterle et al. |
| 2004/0242926 A1 | 12/2004 | Dieterle et al. |

FOREIGN PATENT DOCUMENTS

| DE | 199 10 506 A1 | 9/2000 |
|---|---|---|
| DE | 199 27 624 A1 | 12/2000 |
| DE | 199 48 241 A1 | 4/2001 |
| DE | 199 48 248 A1 | 4/2001 |
| DE | 199 48 523 A1 | 4/2001 |
| EP | 1 106 598 A2 | 6/2001 |
| WO | WO 00/53556 | 9/2000 |
| WO | WO 01/36364 A1 | 5/2001 |

OTHER PUBLICATIONS

U.S. Appl. No. 10/912,075, filed Aug. 6, 2004, Schliephake et al.
U.S. Appl. No. 10/784,825, filed Feb. 24, 2004, Petzoldt et al.
U.S. Appl. No. 10/934,624, filed Sep. 7, 2004, Borgmeier et al.
U.S. Appl. No. 10/920,428, filed Aug. 18, 2004, Borgmeier et al.
U.S. Appl. No. 10/799,754, filed Mar. 15, 2004, Dieterle et al.
U.S. Appl. No. 10/808,282, filed Mar. 25, 2004, Petzoldt et al.
U.S. Appl. No. 10/784,778, filed Feb. 24, 2004, Dieterle et al.
U.S. Appl. No. 10/803,897, filed Mar. 19, 2004, Dieterle et al.
U.S. Appl. No. 10/784,825, filed Feb. 24, 2004, Petzoldt et al.
U.S. Appl. No. 10/806,460, filed Mar. 23, 2004, Dieterle et al.

*Primary Examiner*—Taylor Victor Oh
(74) *Attorney, Agent, or Firm*—Oblon, Spivak, McClelland, Maier & Neustadt, P.C.

(57) ABSTRACT

In a process for heterogeneously catalyzed partial gas phase oxidation of propene to acrolein, the starting reaction gas mixture is oxidized over a fixed catalyst bed which consists of at least two fixed catalyst bed zones and is accommodated in two successive temperature zones A, B, and the transition from temperature zone A to temperature zone B does not spatially coincide with a transition from one fixed catalyst bed zone to another fixed catalyst bed zone.

18 Claims, No Drawings

HETEROGENEOUSLY CATALYZED PARTIAL GAS PHASE OXIDATION OF PROPENE TO ACROLEIN

The present invention relates to a process for partially oxidizing propene to acrolein in the gas phase under heterogeneous catalysis by conducting a starting reaction gas mixture which comprises propene, molecular oxygen and at least one inert gas, and contains the molecular oxygen and the propene in a molar $O_2:C_3H_6$ ratio of $\geq 1$ in a reaction stage over a fixed catalyst bed whose active composition is at least one multimetal oxide comprising the elements Mo, Fe and Bi, in such a way that the fixed catalyst bed is arranged in two spatially successive temperature zones A, B, both the temperature of temperature zone A and the temperature of temperature zone B are a temperature in the range from 290 to 380° C., the fixed catalyst bed consists of at least two spatially successive fixed catalyst bed zones, and the volume-specific activity within one fixed catalyst bed zone is substantially constant and increases sharply in the flow direction of the reaction gas mixture at the transition from one fixed catalyst bed zone to another fixed catalyst bed zone, the temperature zone A extends up to a conversion of the propene of from 40 to 80 mol %, on single pass of the starting reaction gas mixture through the entire fixed catalyst bed, the propene conversion is $\geq 90$ mol % and the selectivity of acrolein formation based on converted propene is $\geq 90$ mol %, the sequence in time in which the reaction gas mixture flows through the temperature zones A, B corresponds to the alphabetic sequence of the temperature zones, the hourly space velocity of the propene contained in the starting reaction gas mixture on the fixed catalyst bed is $\geq 90$ l (STP) of propene/l of fixed bed catalyst·h the difference $T^{maxA}-T^{maxB}$, formed from the highest temperature $T^{maxA}$ which the reaction gas mixture has within temperature zone A, and the highest temperature $T^{maxB}$ which the reaction gas mixture has within temperature zone B is $\geq 0°$ C.

The abovementioned process for partially oxidizing propene to acrolein under heterogeneous catalysis is known in principle, for example, from WO 00/53556 and is of particular importance as a first oxidation stage in the preparation of acrylic acid by two-stage catalytic gas phase oxidation starting from propene. Acrylic acid is an important monomer which finds use as such or in the form of its acrylic ester for obtaining polymers suitable, for example, as adhesives.

In addition to molecular oxygen and the reactants, the starting reaction gas mixture contains inert gas in order to keep the reaction gas outside the explosion range, among other reasons.

One objective of such a catalyzed partial gas phase oxidation of propene to acrolein is to achieve a very high selectivity $S^{AC}$ for acrolein (this is the number of moles of propene converted to acrolein, based on the number of moles of converted propene) on single pass of the reaction gas mixture through the reaction stage under otherwise predefined boundary conditions.

A further objective is to achieve a very high conversion $C^P$ of propylene (this is the number of moles of converted propene, based on the number of moles of propene used) on single pass of the reaction gas mixture through the reaction stages under otherwise identical boundary conditions.

When the $S^{AC}$ is high at high $C^P$, this corresponds to a high yield $Y^{AC}$ of acrolein ($Y^{Ac}$ is the product $C^P \cdot S^{AC}$; i.e. the number of moles of propene converted to acrolein, based on the number of moles of propene used).

A further objective of such a heterogeneously catalyzed partial gas phase oxidation of propene to acrolein is to achieve a very high space-time yield ($STY^{AC}$) of acrolein (in a continuous process, this is the total amount of acrolein obtained per hour and unit volume of the fixed catalyst bed used in liters).

At a constant given yield $Y^{AC}$, the greater the hourly space velocity of propene on the fixed catalyst bed of the reaction stage (this refers to the amount of propene in liters at STP (=l (STP); the volume in liters which would be taken up by the appropriate amount of propene under standard conditions, i.e. at 25° C. and 1 bar) which is conducted as a constituent of the starting reaction gas mixture through one liter of fixed catalyst bed per hour), the higher the space-time yield.

DE-A 19948241, DE-A 19910506 and WO 0053556 teach that the abovementioned aims can indeed be achieved in principle by means of the process described at the outset for heterogeneously catalyzed partial gas phase oxidation of propene to acrolein.

This is advantageous in that a low volume-specific activity can be achieved within a fixed catalyst bed or fixed catalyst bed zone, for example, by diluting the actual shaped catalyst bodies bearing the active composition with inert shaped diluent bodies free of active composition, which makes the fixed catalyst bed less expensive overall.

However, a disadvantage of the teachings of DE-A 19948241, of DE-A 19910506 and of WO 00/53556 is that they have no appropriate implementation example and thus leave open the specific configuration of such a procedure.

In a similar manner, EP-A 1106598 teaches a process for heterogeneously catalyzed partial gas phase oxidation of propene to acrolein, in which the fixed catalyst bed of the reaction stage consists of a plurality of spatially successive fixed catalyst bed zones whose volume-specific activity is substantially constant within one fixed catalyst bed zone and increases sharply in the flow direction of the reaction gas mixture at the transition from one fixed catalyst bed zone to another fixed catalyst bed zone and may be arranged in a plurality of temperature zones.

According to the teaching of EP-A 1106598, it is advantageous when fixed catalyst bed zones and temperature zones spatially coincide.

However, detailed in-house investigations have shown that spatial coincidence of fixed catalyst bed zones and temperature zones is generally not beneficial for optimum achievement of the different objectives referred to.

Among other factors, this can be attributed to the transition from temperature zone A to temperature zone B and the transition from one fixed catalyst bed zone to another fixed catalyst bed zone being taken as substantially coactive or as substantially counteractive measures.

When they are taken at substantially coactive measures (for example, transition from a colder temperature zone A to a hotter temperature zone B and transition from a fixed catalyst bed zone having lower volume-specific activity to a fixed catalyst bed zone having higher volume-specific activity; both measures have the purpose of supporting the reaction), the overall effect achieved in the transition region frequently overshoots the aim pursued and this results, for example, in a reduction of $S^{AC}$.

When they are taken as substantially counteractive measures (for example, transition from a hotter temperature zone A to a colder temperature zone B and transition from a fixed catalyst bed zone having lower volume-specific activity to a fixed catalyst bed zone having higher volume-specific activity; the first measure has the purpose of reducing the reaction, the second measure has the purpose of supporting the reaction), the effects frequently neutralize each other in the transition region, resulting in a reduced $C^P$.

It is an object of the present invention to provide a process for heterogeneously catalyzed partial gas phase oxidation of propene to acrolein in a multizone arrangement, which does not have the disadvantages of the prior art.

We have found that this object is achieved by a process for partially oxidizing propene to acrolein in the gas phase under heterogeneous catalysis by conducting a starting reaction gas mixture comprising propene, molecular oxygen and at least one inert gas, and contains the molecular oxygen and the propene in a molar $O_2:C_3H_6$ ratio of $\geq 1$, in a reaction stage over a fixed catalyst bed whose active composition is at least one multimetal oxide comprising the elements Mo, Fe and Bi, in such a way that the fixed catalyst bed is arranged in two spatially successive temperature zones A, B, both the temperature of temperature zone A and the temperature of temperature zone B are a temperature in the range from 290 to 380° C., the fixed catalyst bed consists of at least two spatially successive fixed catalyst bed zones, and the volume-specific activity within one fixed catalyst bed zone is substantially constant and increases sharply in the flow direction of the reaction gas mixture at the transition from one fixed catalyst bed zone to another fixed catalyst bed zone, the temperature zone A extends up to a conversion of the propene of from 40 to 80 mol %, on single pass of the starting reaction gas mixture through the entire fixed catalyst bed, the propene conversion is $\geq 90$ mol % and the selectivity of acrolein formation based on converted propene is $\geq 90$ mol %, the sequence in time in which the reaction gas mixture flows through the temperature zones A, B corresponds to the alphabetic sequence of the temperature zones, the hourly space velocity of the propene contained in the starting reaction gas mixture on the fixed catalyst bed is $\geq 90$ l (STP) of propene/l of fixed bed catalyst·h the difference $T^{maxA}-T^{maxB}$, formed from the highest temperature $T^{maxA}$ which the reaction gas mixture has within temperature zone A, and the highest temperature $T^{maxB}$ which the reaction gas mixture has within temperature zone B is $\geq 0°$ C., wherein the transition from temperature zone A to temperature zone B in the fixed catalyst bed (spatially) does not coincide with a transition from one fixed catalyst bed zone to another fixed catalyst bed zone.

In this document, the temperature of a temperature zone refers to the temperature of the portion of the fixed catalyst bed disposed in the temperature zone when practising the process according to the invention, except in the absence of a chemical reaction. When this temperature is not constant within the temperature zone, the term temperature of a temperature zone then refers to the (numerical) mean of the temperature of the fixed catalyst bed along the temperature zone. It is essential that the heating of the individual temperature zones is substantially independent.

Since the heterogeneously catalyzed partial gas phase oxidation of propene to acrolein is a distinctly exothermic reaction, the temperature of the reaction gas mixture on reactive pass through the fixed catalyst bed is generally different from the temperature of a temperature zone. They are normally above the temperature of the temperature zone and generally pass through a maximum (heating point maximum) or fall starting from a maximum value within a temperature zone.

In general, the difference $T^{maxA}-T^{maxB}$ in the process according to the invention will not be more than 80° C. According to the invention, $T^{maxA}-T^{maxB}$ is preferably $\geq 3°$ C. and $\leq 70°$ C. With very particular preference, $T^{maxA}-T^{maxB}$ in the process according to the invention is $\geq 20°$ C. and $\leq 60°$ C.

When practising the process according to the invention in the case of relatively low ($\geq 90$ l (STP)/l·h and $\leq 160$ l (STP)/l·h) catalyst velocities of propene on the fixed catalyst bed, the $T^{maxA}-T^{maxB}$ differences required according to the invention are normally attained when, on the one hand, both the temperature of temperature zone A and the temperature of temperature zone B are in the range from 290 to 380° C. and, on the other hand, the difference between the temperature of temperature zone B ($T_B$) and the temperature of temperature zone A ($T_A$), i.e., $T_B-T_A$, is $\leq 0°$ C. and $\geq -20°$ C. or $\geq -10°$ C. or $\leq 0°$ C. and $\geq -5°$ C., or frequently $\leq 0°$ C. and $\geq -3°$ C.

When practising the process according to the invention under increased propene catalyst velocities ($\geq 160$ l (STP)/l·h and $\leq 300$ l (STP)/l·h, or $\leq 600$ l (STP)/l·h), the $T^{maxA}-T^{maxB}$ differences required according to the invention are normally attained when, on the one hand, both the temperature of temperature zone A and the temperature of temperature zone B are in the range from 290 to 380° C. and $T_B-T_A$ is $\geq 0°$ C. and $\leq 50°$ C., or $\geq 5°$ C. and $\leq 45°$ C, or $\geq 10°$ C. and $\leq 40°$ C., or $\geq 15°$ C. and $\leq 30°$ C. or $\leq 35°$ C. (e.g. 20° C. or 25° C.).

The above statement regarding the $T_B-T_A$ temperature differences regularly also applies when the temperature of temperature zone A is within the preferred range of from 305 to 365° C. or in the particularly preferred range of from 310 to 340° C.

The hourly space velocity of propene on the fixed catalyst bed in the process according to the invention may therefore be, for example, $\geq 90$ l (STP)/l·h and $\leq 300$ l (STP)/l·h, or $\geq 110$ l (STP)/l·h and $\leq 280$ l (STP)/l·h or $\geq 130$ l (STP)/l·h and $\leq 260$ l (STP)/l·h, or $\geq 150$ l (STP)/l·h and $\leq 240$ l (STP)/l·h, or $\geq 170$ l (STP)/l·h and $\leq 220$ l (STP)/l·h, or $\geq 190$ l (STP)/l·h and $\leq 200$ l (STP)/l·h.

According to the invention, temperature zone A preferably extends up to a propene conversion of from 50 to 70 mol % or from 60 to 70 mol %.

The working pressure in the process according to the invention can be either below atmospheric pressure (e.g. down to 0.5 bar) or above atmospheric pressure. Typically, the working pressure will be at values of from 1 to 5 bar, frequently from 1 to 3 bar. Normally, the reaction pressure will not exceed 100 bar.

In general, the propene conversion in the process according to the invention based on a single pass will be $\geq 92$ mol % or $\geq 94$ mol % or $\geq 96$ mol %. The selectivity of acrolein formation will regularly be $\geq 92$ mol %, or $\geq 94$ mol %, frequently $\geq 95$ mol %, or $\geq 96$ mol % or $\geq 97$ mol %.

Useful sources for the molecular oxygen required are both air and air depleted of molecular nitrogen.

Useful catalysts for the fixed catalyst bed of the process according to the invention include all of those catalysts whose active composition is at least one multimetal oxide comprising Mo, Bi and Fe.

These are in particular the multimetal oxide active compositions of the general formula I of DE-A 19955176, the multimetal oxide active compositions of the general formula I of DE-A 19948523, the multimetal oxide active compositions of the general formulae I, II and III of DE-A 10101695, the multimetal oxide active compositions of the general formulae I, II and III of DE-A 19948248 and the multimetal oxide active compositions of the general formulae I, II and III of DE-A 19955168 and also the multimetal oxide active compositions specified in EP-A 700714.

Also suitable for the fixed catalyst bed are the multimetal oxide catalysts comprising Mo, Bi and Fe which are disclosed in the documents DE-A 10046957, DE-A 10063162, DE-C 3338380, DE-A 19902562, EP-A 15565, DE-C 2380765, EP-A 807465, EP-A 279374, DE-A 3300044, EP-A 575897, U.S. Pat. No. 4,438,217, DE-A 19855913, WO 98/24746, DE-A 19746210 (those of the general formula II), JP-A 91/294239, EP-A 293224 and EP-A 700714. This applies in particular for the exemplary embodiments in these documents, and among these particular preference is given to those of EP-A 15565, EP-A 575897, DE-A 19746210 and DE-A 19855913. Particular emphasis is given in this context to a catalyst according to example 1 c from EP-A 15565 and also to a catalyst to be prepared in a corresponding manner but having the active composition $Mo_{12}Ni_{6.5}Zn_2Fe_2Bi_1P_{0.0065}K_{0.06}Ox \cdot 10\ SiO_2$. Emphasis is also given to the example having the serial number 3 from DE-A 19855913 (stoichiometry: $Mo_{12}Co_7Fe_3Bi_{0.6}K_{0.08}Si_{1.6}Ox$) as an unsupported hollow cylinder catalyst of geometry 5 mm×3 mm×2 mm or 5 mm×2 mm×2 mm (each external diameter×height×internal diameter) and also to the unsupported multimetal oxide II catalyst according to example 1 of DE-A 19746210. Mention should also be made of the multimetal oxide catalysts of U.S. Pat. No. 4,438,217. The latter is true in particular when these have a hollow cylinder geometry of the dimensions 5.5 mm×3 mm×3.5 mm, or 5 mm×2 mm×2 mm, or 5 mm×3 mm×2 mm, or 6 mm×3 mm×3 mm, or 7 mm×3 mm×4 mm (each external diameter×height×internal diameter). Likewise suitable are the multimetal oxide catalysts and geometries of DE-A 10101695 or WO 02/062737.

Also suitable are example 1 of DE-A 10046957 (stoichiometry: $[Bi_2W_2O_9x \cdot 2WO_3]_{0.5} \cdot [Mo_{12}Co_{5.6}Fe_{2.94}Si_{1.59}K_{0.08}O_x]_1$) as an unsupported hollow cylinder (ring) catalyst of geometry 5 mm×3 mm×2 mm or 5 mm×2 mm×2 mm (each external diameter×length×internal diameter), and also the coated catalysts 1, 2 and 3 of DE-A 10063162 (stoichiometry: $Mo_{12}Bi_{1.0}Fe_3Co_7Si_{1.6}K_{0.08}$), except as annular coated catalysts of appropriate coating thickness and applied to support rings of geometry 5 mm×3 mm×1.5 mm or 7 mm×3 mm×1.5 mm (each external diameter×length×internal diameter).

A multiplicity of the multimetal oxide active compositions suitable for the catalysts of the fixed catalyst bed can be encompassed by the general formula I $$Mo_{12}Bi_aFe_bX^1_cX^2_dX^3_eX^4_fO_n \qquad (I)$$

where the variables are defined as follows:

$X^1$=nickel and/or cobalt,
$X^2$=thallium, an alkali metal and/or an alkaline earth metal,
$X^3$=zinc, phosphorus, arsenic, boron, antimony, tin, cerium, lead and/or tungsten,
$X^4$=silicon, aluminum, titanium and/or zirconium,
a=from 0.5 to 5,
b=from 0.01 to 5, preferably from 2 to 4,
c=from 0 to 10, preferably from 3 to 10,
d=from 0 to 2, preferably from 0.02 to 2,
e=from 0 to 8, preferably from 0 to 5,
f=from 0 to 10 and
n=a number which is determined by the valency and frequency of the elements in I other than oxygen.

They are obtainable in a manner known per se (see, for example, DE-A 4023239) and are customarily shaped undiluted to give spheres, rings or cylinders or else used in the form of coated catalysts, i.e. preshaped inert support bodies coated with the active composition. It will be appreciated that they may also be used as catalysts in powder form.

In principle, active compositions of the general formula I can be prepared in a simple manner by obtaining a very intimate, preferably finely divided dry mixture corresponding to their stoichiometry from suitable sources of their elemental constituents and calcining it at temperatures of from 350 to 650° C. The calcination may be effected either under inert gas or under an oxygen atmosphere, for example air (mixture of inert gas and oxygen) and also under a reducing atmosphere (for example mixture of inert gas, $NH_3$, CO and/or $H_2$). The calcination time can be from a few minutes to a few hours and typically decreases with temperature. Useful sources for the elemental constituents of the multimetal oxide active compositions I are those compounds which are already oxides and/or those compounds which can be converted to oxides by heating, at least in the presence of oxygen.

In addition to the oxides, such useful starting compounds include in particular halides, nitrates, formates, oxalates, citrates, acetates, carbonates, amine complexes, ammonium salts and/or hydroxides (compounds such as $NH_4OH$, $(NH_4)_2CO_3$, $NH_4NO_3$, $NH_4CHO_2$, $CH_3COOH$, $NH_4CH_3CO_2$ and/or ammonium oxalate, which decompose and/or can be decomposed on later calcining at the latest to release compounds in gaseous form can be additionally incorporated into the intimate dry mixture).

The starting compounds for preparing the multimetal oxide active compositions I can be intimately mixed in dry or in wet form. When they are mixed in dry form, the starting compounds are advantageously used as finely divided powders and subjected to calcination after mixing and optional compacting. However, preference is given to intimate mixing in wet form. Customarily, the starting compounds are mixed with each other in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

Typically, the multimetal oxide active compositions of the general formula I are used in the fixed catalyst bed not in powder form, but rather shaped into certain catalyst geometries, and the shaping may be effected either before or after the final calcination. For example, unsupported catalysts can be prepared from the powder form of the active composition or its uncalcined and/or partially calcined precursor composition by compacting to the desired catalyst geometry (for example by tableting or extruding), optionally with the addition of assistants, for example graphite or stearic acid as lubricants and/or shaping assistants and reinforcing agents such as microfibers of glass, asbestos, silicon carbide or potassium titanate. Examples of unsupported catalyst geometries include solid cylinders or hollow cylinders having an external diameter and a length of from 2 to 10 mm. In the case of the hollow cylinder, a wall thickness of from 1 to 3 mm is advantageous. It will be appreciated that the unsupported catalyst can also have spherical geometry, and the spherical diameter can be from 2 to 10 mm.

A particularly advantageous hollow cylinder geometry is 5 mm×3 mm×2 mm (external diameter×length×internal diameter), in particular in the case of unsupported catalysts.

It will be appreciated that the pulverulent active composition or its pulverulent precursor composition which is yet to be calcined and/or partially calcined can be shaped by applying to preshaped inert catalyst supports. The coating of the support bodies to produce the coated catalysts is generally performed in a suitable rotatable vessel, as disclosed, for example, by DE-A 2909671, EP-A 293859 or EP-A 714700. To coat the support bodies, the powder composition to be applied is advantageously moistened and dried again after application, for example by means of hot air. The coating thickness of the powder composition applied to the support body is advantageously selected within the range from 10 to 1 000 μm, preferably within the range from 50 to 500 μm and more preferably within the range from 150 to 250 μm.

Useful support materials are the customary porous or nonporous aluminum oxides, silicon dioxide, thorium dioxide, zirconium dioxide, silicon carbide or silicates such as magnesium silicate or aluminum silicate. They generally behave inertly with regard to the target reaction on which the process according to the invention in the first reaction stage is based. The support bodies may have a regular or irregular shape, although preference is given to regularly shaped support bodies having a distinct surface roughness, for example spheres or hollow cylinders. It is suitable to use substantially nonporous, surface-roughened spherical supports made of steatite (e.g. Steatite C220 from CeramTec) whose diameter is from 1 to 8 mm, preferably from 4 to 5 mm. However, suitable support bodies also include cylinders whose length is from 2 to 10 mm and whose external diameter is from 4 to 10 mm. In the case of rings suitable as support bodies according to the invention, the wall thickness is also typically from 1 to 4 mm. According to the invention, annular support bodies to be used preferably have a length of from 2 to 6 mm, an external diameter of from 4 to 8 mm and a wall thickness of from 1 to 2 mm. Suitable as support bodies according to the invention are in particular rings of geometry 7 mm×3 mm×4 mm (external diameter×length× internal diameter). It will be appreciated that the fineness of the catalytically active oxide compositions to be applied to the surface of the support body will be adapted to the desired coating thickness (cf. EP-A 714 700).

Suitable multimetal oxide active compositions for the catalysts of the reaction stage are also compositions of the general formula II

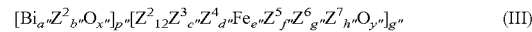
(II)

where the variables are defined as follows:
$Y^1$=only bismuth or bismuth and at least one of the elements tellurium, antimony, tin and copper,
$Y^2$=molybdenum or molybdenum and tungsten,
$Y^3$=an alkali metal, thallium and/or samarium,
$Y^4$=an alkaline earth metal, nickel, cobalt, copper, manganese, zinc, tin, cadmium and/or mercury,
$Y^5$=iron or iron and at least one of the elements chromium and cerium,
$Y^6$=phosphorus, arsenic, boron and/or antimony,
$Y^7$=a rare earth metal, titanium, zirconium, niobium, tantalum, rhenium, ruthenium, rhodium, silver, gold, aluminum, gallium, indium, silicon, germanium, lead, thorium and/or uranium,
a'=from 0.01 to 8,
b'=from 0.1 to 30,
c'=from 0 to 4,
d'=from 0 to 20,
e'=from 0 to 20,
f'=from 0 to 6,
g'=from 0 to 15,
h'=from 8 to 16,
x',y'=numbers which are determined by the valency and frequency of the elements in II other than oxygen and
p,q=numbers whose p/q ratio is from 0.1 to 10, comprising three-dimensional regions of the chemical composition $Y^1_{a'} Y^2_{b'} O_{x'}$ which are delimited from their local environment as a consequence of their different chemical composition from their local environment, and whose maximum diameter (longest line cutting through the center of the region and connecting two points on the surface (interface) of the region) is from 1 nm to 100 μm, frequently from 10 nm to 500 nm or from 1 μm to 50 or 25 μm.

Particularly advantageous multimetal oxide compositions II according to the invention are those in which $Y^1$ is only bismuth.

Among these, preference is given in turn to those of the general formula III

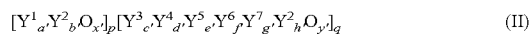
(III)

where the variables are defined as follows:
$Z^2$=molybdenum or molybdenum and tungsten,
$Z^3$=nickel and/or cobalt,
$Z^4$=thallium, an alkali metal and/or an alkaline earth metal,
$Z^5$=phosphorus, arsenic, boron, antimony, tin, cerium and/or lead,
$Z^6$=silicon, aluminum, titanium and/or zirconium,
$Z^7$=copper, silver and/or gold,
a"=from 0.1 to 1,
b"=from 0.2 to 2,
c"=from 3 to 10,
d"=from 0.02 to 2,
e"=from 0.01 to 5, preferably from 0.1 to 3,
f"=from 0 to 5,
g"=from 0 to 10,
h"=from 0 to 1,
x",y"=numbers which are determined by the valency and frequency of the elements in III other than oxygen,
p",q"=numbers whose p"/q" ratio is from 0.1 to 5, preferably from 0.5 to 2, and particular preference is given to those compositions III in which $Z^2_{b''}$=(tungsten)$_{b''}$ and $Z^2_{12}$=(molybdenum)$_{12}$.

It is also advantageous when at least 25 mol % (preferably at least 50 mol % and more preferably at least 100 mol %) of the total proportion of $[Y^1_{a'}Y^2_{b'}O_{x'}]_p$ ($[Bi_{a''}Z^2_{b''}O_{x''}]_{p''}$) of the multimetal oxide compositions II (multimetal oxide compositions II) suitable according to the invention in the multimetal oxide compositions II (multimetal oxide compositions III) suitable according to the invention are in the form of three-dimensional regions of the chemical composition $Y^1_{a'}Y^2_{b'}[Bi_{a''}Z^2_{b''}O_{x''}]$ which are delimited from their local environment as a consequence of their different chemical composition from their local environment, and whose maximum diameter is in the range from 1 nm to 100 μm.

With regard to the shaping, the statements made for the multimetal oxide I catalysts apply to the multimetal oxide II catalysts. The preparation of multimetal oxide II active compositions is described, for example, in EP-A 575897 and also in DE-A 19855913.

It is essential to the invention that the fixed catalyst bed consists of at least two spatially successive fixed catalyst bed zones, and the volume-specific activity within one fixed catalyst bed zone is substantially constant and increases sharply in the flow direction of the reaction gas mixture at the transition from one fixed catalyst bed zone to another fixed catalyst bed zone.

The volume-specific (i.e. normalized to the unit of the particular bed volume) activity of a fixed bed catalyst zone can then be adjusted over the fixed catalyst bed zone in a substantially constant manner by starting from a basic amount of shaped catalyst bodies prepared in a uniform manner (their bed corresponds to the maximum achievable volume-specific activity) and homogeneously diluting it in the particular fixed catalyst bed zone with shaped bodies (shaped diluent bodies) which behave substantially inertly with regard to the heterogeneously catalyzed partial gas phase oxidation. The higher the proportion of shaped diluent bodies selected, the less active composition and catalyst activity, present in a certain volume of the bed. Useful materials for such inert shaped diluent bodies are in principle all of those which are suitable as support material for coated catalysts suitable according to the invention.

Useful such materials include, for example, porous or nonporous aluminum oxides, silicon dioxide, thorium dioxide, zirconium dioxide, silicon carbide, silicates such as magnesium silicate or aluminum silicate or the steatite already mentioned above (e.g. Steatite C-220 from CeramTec).

The geometry of such inert shaped diluent bodies may in principle be as desired. In other words, they may, for example, be spheres, polygons, solid cylinders or else rings. According to the invention, the inert shaped diluent bodies selected will preferably be those whose geometry corresponds to that of the shaped catalyst bodies to be diluted with them.

According to the invention, it is advantageous when the chemical composition of the active composition used does not vary over the entire fixed catalyst bed. In other words, although the active composition used for a single shaped catalyst body can be a mixture of different multimetal oxides comprising the elements Mo, Fe and Bi, the same mixture then has to be used for all shaped catalyst bodies of the fixed catalyst bed.

A volume-specific activity increasing zone by zone over the fixed catalyst bed in the flow direction of the reaction gas mixture can therefore be achieved for the process according to the invention in a simple manner, for example, by beginning the bed in a first fixed catalyst bed zone with a high proportion of inert shaped diluent bodies based on one type of shaped catalyst bodies, and then reducing this proportion of shaped diluent bodies zone by zone in the flow direction.

However, a zone by zone increase in the volume-specific activity is also possible, for example, by increasing the thickness of the active composition layer applied to the support zone by zone at constant geometry and active composition type of a coated shaped catalyst body or, in a mixture of coated catalysts having the same geometry but having different proportions by weight of the active composition by increasing the proportion of shaped catalyst bodies having higher proportions by weight of active composition zone by zone. Alternatively, the active compositions themselves can be diluted in the course of the active composition preparation by, for example, incorporating inert, diluting materials such as hard-fired silica into the dry mixture of starting compounds to be calcined. Different amounts of diluting material added lead automatically to different activities. The more diluting material is added, the lower the resulting activity will be. A similar effect can also be achieved, for example, in the case of mixtures of unsupported catalysts and of coated catalysts (having identical active composition) by varying the mixing ratio in an appropriate manner. A variation in the volume-specific activity can also be achieved by the use of catalyst geometries having different bed densities (for example, in the case of unsupported catalysts having identical active compositions of the different geometries). It will be appreciated that the variants described can also be used in combination.

It is of course also possible to use mixtures of catalysts having chemically different active compositions and, as a consequence of these different compositions, having different activities for the fixed catalyst bed. These mixtures may in turn, zone by zone, be varied in their composition and/or be diluted with different amounts of inert shaped diluent bodies.

Upstream and/or downstream of the fixed catalyst bed may be disposed beds consisting exclusively of inert material (for example only shaped diluent bodies) (in this document, they are not included for terminology purposes in the fixed catalyst bed, since they contain no shaped bodies which have multimetal oxide active composition). The shaped diluent bodies used for the inert bed can have the same geometry as the shaped catalyst bodies used in the fixed catalyst bed. However, the geometry of the shaped diluent bodies used for the inert bed may also be different to the abovementioned geometry of the shaped catalyst bodies (for example, spherical instead of annular).

Frequently, the shaped bodies used for such inert beds have the annular geometry 7 mm×7 mm×4 mm (external diameter×length×internal diameter) or the spherical geometry having a diameter d=4–5 mm. Temperature zones A and B in the process according to the invention may also extend to the inert beds. According to the invention, it is advantageous when neither temperature zone A nor temperature zone B covers more than three fixed catalyst bed zones (according to the invention, at least one fixed catalyst bed zone is necessarily covered by both temperature zones).

According to the invention, it is particularly advantageous when the entire fixed catalyst bed comprises not more than five, advantageously not more than four or three fixed catalyst bed zones.

According to the invention, at the transition from one fixed catalyst bed zone to another fixed catalyst bed zone (in the flow direction of the reaction gas mixture), the volume-specific active composition (i.e. the weight of the multimetal oxide composition present in the uniform bed volume) should (in the case of uniform active composition over the entire fixed catalyst bed) advantageously increase by at least 5% by weight, preferably by at least 10% by weight (this applies in particular in the case of uniform shaped catalyst bodies over the entire fixed catalyst bed). In general, this increase in the process according to the invention will not be more than 50% by weight, usually not more than 40% by weight. According to the invention, in the case of uniform active composition over the entire fixed catalyst bed, the difference in the volume-specific active composition of the fixed catalyst bed zone having the lowest volume-specific activity and the fixed catalyst bed zone having the highest volume-specific activity should also advantageously not be more than 50% by weight, preferably not more than 40% by weight, and generally not more than 30% by weight.

In the process according to the invention, the fixed catalyst bed will frequently consist of only two fixed catalyst bed zones.

According to the invention, preference is given to the last fixed catalyst bed zone in the flow direction of the reaction gas mixture being undiluted. In other words, it preferably consists exclusively of shaped catalyst bodies. If required, it may also consist of a bed of shaped catalyst bodies whose volume-specific activity is reduced, for example by dilution with inert material, for example by 10%.

When the fixed catalyst bed consists of only two fixed catalyst bed zones, it is generally advantageous according to the invention (as is quite generally the case in the process according to the invention) when the fixed catalyst bed zone having the highest volume-specific activity does not extend into temperature zone A (in particular when the heating is effected in temperature zone A and temperature zone B by means of a flowing heat carrier which in each case flows in countercurrent to the reaction gas mixture). In other words, the fixed catalyst bed zone having the lower volume-specific activity will extend into temperature zone B and the fixed catalyst bed zone having the higher volume-specific activity will begin and end in temperature zone B (i.e. have its beginning beyond the transition from temperature zone A to temperature zone B).

When the fixed catalyst bed consists of only three fixed catalyst bed zones, it is generally advantageous according to the invention when the fixed catalyst bed zone having the highest volume-specific activity does not extend into temperature zone A but begins and ends in temperature zone B, i.e. has its beginning beyond the transition from temperature zone A to temperature zone B (in particular when the heating in temperature zone A and temperature zone B is effected by means of a flowing heat carrier which in each case flows in countercurrent to the reaction gas mixture). In other words, the fixed catalyst bed zone having the second highest volume-specific activity will normally extend both into temperature zone A and temperature zone B.

When the fixed catalyst bed consists of four fixed catalyst bed zones, it is generally advantageous in accordance with the invention when the fixed catalyst bed zone having the third highest volume-specific activity extends both into temperature zone A and into temperature zone B (in particular when temperature zone A and temperature zone B are heated by means of a flowing heat carrier which in each case flows in countercurrent to the reaction gas mixture).

In the case of cocurrent flow of reaction gas mixture and heat carriers in temperature zones A and B, it may be advantageous in the process according to the invention if the fixed catalyst bed zone having the highest volume-specific activity extends into temperature zone A.

Generally, the volume-specific activity between two fixed catalyst bed zones can be differentiated experimentally in a simple manner by passing the same propene-containing starting reaction gas mixture over fixed catalyst beds of the same length but each corresponding to the composition of the particular fixed catalyst bed zone under identical boundary conditions (preferably the conditions of the contemplated process). The higher amount of propene converted indicates the higher volume-specific activity.

When the total length of the fixed catalyst bed is $L^1$, it is advantageous in accordance with the invention if there is no transition from one fixed catalyst bed zone to another fixed catalyst bed zone within the region of $$X \pm L \cdot \frac{4}{100}$$

or within the region of $$X \pm L \cdot \frac{3}{100}$$

or within the region of $$X \pm L \cdot \frac{2}{100}$$

where X is the location (the position) within the fixed catalyst bed of the transition from temperature zone A to temperature zone B.

Preference is given in accordance with the invention to the fixed catalyst bed in the process according to the invention being structured as follows in the flow direction of the reaction gas mixture.

First, to a length of from 10 to 60%, preferably from 10 to 50%, more preferably from 20 to 40% and most preferably from 25 to 35% (i.e., for example, to a length of from 0.70 to 1.50 m, preferably from 0.90 to 1.20 m), each of the total length of the fixed catalyst bed 1, a homogeneous mixture of shaped catalyst bodies and shaped diluent bodies (both preferably having substantially the same geometry), in which the proportion by weight of the shaped diluent bodies (the densities of shaped catalyst bodies and of shaped diluent bodies generally differ only slightly) is normally from 5 to 40% by weight, or from 10 to 40% by weight, or from 20 to 40% by weight, or from 25 to 35% by weight. According to the invention, this first zone of the fixed catalyst bed is advantageously followed up to the end of the length of the fixed catalyst bed (i.e., for example, to a length of from 2.00 to 3.00 m, preferably from 2.50 to 3.00 m) either by a bed of shaped catalyst bodies diluted only to a slighter extent (than in the first zone), or, most preferably, an unaccompanied (undiluted) bed of the same shaped catalyst bodies which have also been used in the first zone. The aforesaid applies in particular when the shaped catalyst bodies used in the fixed catalyst bed are unsupported catalyst rings or coated catalyst rings (in particular those which are specified as preferred in this document). For the purposes of the abovementioned structuring, both the shaped catalyst bodies and the shaped diluent bodies in the process according to the invention advantageously have substantially the ring geometry 5 mm×3 mm×2 mm (external diameter×length×internal diameter).

The aforesaid also applies when, instead of inert shaped diluent bodies, shaped coated catalyst bodies are used whose active composition content is from 2 to 15% by weight lower than the active composition content of any shaped coated catalyst bodies used at the end of the fixed catalyst bed.

A pure inert material bed whose length, based on the length of the fixed catalyst bed, is advantageously from 5 to 20% generally precedes the fixed catalyst bed in the flow direction of the reaction gas mixture. It is normally utilized as a heating zone for the reaction gas mixture.

According to the invention, the fixed catalyst bed zone having the lower volume-specific activity in the aforementioned fixed catalyst bed then advantageously extends for from 5 to 20%, frequently from 5 to 15%, of its length into temperature zone B.

According to the invention, temperature zone A also advantageously extends to a preliminary bed of inert material which is optionally used.

In an advantageous manner from an application point of view, the reaction stage according to the invention of the process according to the invention is carried out in a two-zone tube bundle reactor, as described, for example, in DE-A 19910508, 19948523, 19910506 and 19948241. A preferred variant of a two-zone tube bundle reactor which can be used in accordance with the invention is disclosed by DE-C 2830765. However, the two-zone tube bundle reactors disclosed in DE-C 2513405, U.S. Pat. No. 3,147,084, DE-A 2201528, EP-A 383224 and DE-A 2903218 are also suitable for carrying out the first reaction stage of the process according to the invention.

In other words, in the simplest manner, the fixed catalyst bed to be used in accordance with the invention (possibly with downstream and/or upstream inert beds) is disposed in the metal tubes of a tube bundle reactor and two spatially separated heating media, generally salt melts, are conducted around the metal tubes. The tube section over which the particular salt bath extends represents a temperature zone in accordance with the invention. In other words, in the simplest manner, for example, a salt bath A flows around that section of the tubes (temperature zone A) in which propene is oxidatively converted (on single pass) until a conversion in the range from 40 to 80 mol % is achieved, and a salt bath B flows around the section of the tubes (reaction zone B) in which the propene is subsequently oxidatively converted (on single pass) until a conversion value of at least 90 mol % is achieved (if required, the temperature zones A, B to be used in accordance with the invention can be followed by further reaction zones which are maintained at individual temperatures).

It is advantageous from an application point of view if the reaction stage of the process according to the invention includes no further temperature zones. In other words, the salt bath B advantageously flows around the section of the tubes in which propene is subsequently oxidatively converted (on single pass) up to a conversion value of $\geq 90$ mol %, or $\geq 92$ mol %, or $\geq 94$ mol % or more.

Typically, the beginning of the temperature zone B lies beyond the heating point maximum of temperature zone A.

According to the invention, both salt baths A, B can be conducted in cocurrent or in countercurrent through the space surrounding the reaction tubes relative to the flow direction of the reaction gas mixture flowing through the reaction tubes. It will be appreciated that, in accordance with the invention, cocurrent flow may be applied in temperature zone A and countercurrent flow in temperature zone B (or vice versa).

In all of the aforementioned cases, it will be appreciated that a transverse flow can be superimposed on the parallel flow of the salt melt relative to the reaction tubes taking place within the particular temperature zone, so that the individual temperature zone corresponds to a tube bundle reactor as described in EP-A 700714 or in EP-A 700893, which results overall in a meandering flow profile of the heat exchange medium in a longitudinal section through the catalyst tube bundle.

Advantageously, the starting reaction gas mixture in the process according to the invention is fed to the fixed catalyst bed preheated to the reaction temperature.

Typically, the catalyst tubes in the two-zone tube bundle reactors are manufactured from ferritic steel and typically have a wall thickness of from 1 to 3 mm. Their internal diameter is generally from 20 to 30 mm, frequently from 21 to 26 mm. Their length is advantageously from 2 to 4 m, preferably from 2.5 to 3.5 m. In each temperature zone, the fixed catalyst bed occupies at least 60%, or at least 75%, or at least 90%, of the length of the zone. Any remaining length is optionally occupied by an inert bed. It is advantageous from an application point of view for the number of catalyst tubes accommodated in the tube bundle vessel to be at least 5 000, preferably at least 10 000. Frequently, the number of catalyst tubes accommodated in the reaction vessel is from 15 000 to 30 000. Tube bundle reactors having a number of catalyst tubes above 40 000 are usually exceptional. Within the vessel, the catalyst tubes are normally homogeneously distributed (preferably 6 equidistant adjacent tubes per catalyst tube), and the distribution is advantageously selected in such a way that the separation of the central internal axes of immediately adjacent catalyst tubes (the catalyst tube pitch) is from 35 to 45 mm (cf., for example, EP-B 468290).

Useful heat exchange media for the two-zone method are also in particular fluid heating media. It is particularly advantageous to use melts of salts such as potassium nitrate, potassium nitrite, sodium nitrite and/or sodium nitrate, or of low-melting metals such as sodium, mercury and also alloys of different metals.

In general, in all of the aforementioned flow arrangements in the two-zone tube bundle reactors, the flow rate within the two heat exchange medium circuits required is selected in such a way that the temperature of the heat exchange medium rises from the entrance into the temperature zone to the exit from the temperature zone (as a result of the exothermicity of the reaction) by from 0 to 15° C. In other words, the aforementioned $\Delta T$ may be from 1 to 10° C., or from 2 to 8° C., or from 3 to 6° C., in accordance with the invention.

According to the invention, the entrance temperature of the heat exchange medium into temperature zone A is normally in the range from 290 to 380° C., preferably in the range from 305 to 365° C. and more preferably in the range from 310 to 340° C. or to 330° C. According to the invention, in the case of propene catalyst velocities on the fixed catalyst bed of $\geq 90$ l (STP)/l·h and <160 l (STP)/l·h, the entrance temperature of the heat exchange medium into temperature zone B is likewise in the range from 290 to 380° C., but at the same time normally, advantageously in accordance with the invention, from $\geq 0$° C. to $\leq 20$° C., or $\leq 10$° C., or $\geq 0$° C. and $\leq 5$° C., or frequently $\geq 0$° C. and $\leq 3$° C., below the entrance temperature of the heat exchange medium entering temperature zone A. According to the invention, in the case of propene catalyst velocities on the fixed catalyst bed of $\geq 160$ l (STP)/l·h and (generally) $\leq 300$ l (STP)/l·h (or 600 l (STP)/l·h), the entrance temperature of the heat exchange medium into temperature zone B will likewise be in the range from 290 to 380° C., but normally, advantageously in accordance with the invention, from $\geq 0$° C. to $\leq 50$° C., or $\geq 5$° C. and $\leq 45$° C., or $\geq 10$° C. and $\leq 40$° C., or $\geq 15$° C. and $\leq 30$° C. or $\leq 35$° C. (for example 20° C. or 25° C.), above the entrance temperature of the heat exchange medium entering temperature zone A.

It is pointed out once again at this juncture that, for an implementation of the reaction stage of the process according to the invention, it is possible to use in particular the two-zone tube bundle reactor type described in DE-B 2201528 which includes the possibility of removing the hotter heat exchange medium of temperature zone B to temperature zone A, in order to optionally heat a cold starting reaction gas mixture or a cold cycle gas. The tube bundle characteristics within an individual temperature zone may also be configured as described in EP-A 382098.

The acrolein can be removed in a manner known per se from the product gas mixture leaving the reaction stage and the remaining gas can be partly recycled in a manner known per se as diluent gas into the propene partial oxidation. However, it will advantageously be used to change a downstream heterogeneously catalyzed partial oxidation of the acrolein contained therein to acrylic acid. Advantageously, it will be cooled in a direct and/or indirect manner before entry into such a downstream reaction stage, in order to thus suppress subsequent full combustion of portions of the acrolein formed in the propene oxidation stage.

An aftercooler is usually connected in between the two reaction stages. In the simplest case, said aftercooler may be an indirect tube bundle heat exchanger. Subsequently, oxygen is usually supplied in the form of air, in order to provide the superstoichiometric oxygen content which is advantageous for such an acrolein oxidation. Such an acrolein partial oxidation is advantageously carried out in a manner similar to the process of the invention.

The propene content in the starting reaction gas mixture in the process according to the invention can, for example, be at values of from 4 to 15% by volume, frequently from 5 to 12% by volume, or from 5 to 8% by volume (based in each case on the total volume).

Frequently, the process according to the invention will be carried out as a propene:oxygen:inert gases (including steam) volume ratio in the starting reaction gas mixture 1 of 1:(1.0 to 3.0):(5 to 25), preferably 1:(1.7 to 2.3):(10 to 15). In general, at least 20% of the volume of the inert gas will consist of molecular nitrogen. However, $\geq 30\%$ by volume, or $\geq 40\%$ by volume, or $\geq 50\%$ by volume, or $\geq 60\%$ by volume, or $\geq 70\%$ by volume, or $\geq 80\%$ by volume, or $\geq 90\%$ by volume, or $\geq 95\%$ by volume, of the inert gas may consist of molecular nitrogen (in this document, inert diluent gases generally refer to those of which less than 5%, preferably less than 2%, is converted on single pass through the reaction stage; in addition to molecular nitrogen, these are, for example, gases such as propane, ethane, methane, pentane, butane, $CO_2$, CO, steam and/or noble gases). Up to 50 mol %, or up to 75 mol % and more of the inert diluent gas in the process according to the invention can consist of propane. Cycle gas, as remains after the removal of the acrolein and/or acrylic acid from the product gas mixture (for example in the case of a downstream second oxidation stage), can also be a constituent of the diluent gas.

The starting reaction gas mixtures which are advantageous according to the invention are, for example, those which are composed of from 6 to 15 (preferably from 7 to 11) % by volume of propene,
from 4 to 20 (preferably from 6 to 12) % by volume of water,
from $\geq 0$ to 10 (preferably from $\geq 0$ to 5) % by volume of constituents other than propene, water, oxygen and nitrogen, sufficient molar oxygen that the molar ratio of molar oxygen present to propene present is from 1.5 to 2.5 (preferably from 1.6 to 2.2), and the remainder up to 100% by volume of the total amount of molecular nitrogen.

as recommended by DE-A 10302715.

It is emphasized at this juncture that the multimetal oxide compositions of DE-A 10261186 are advantageous as active compositons for the fixed catalyst bed.

Designs of a two-zone tube bundle reactor for the reaction stage according to the invention which are advantageous in accordance with the invention can have the following construction (the detailed configuration of the construction can be as described in the utility model applications 202 19 277.6, 2002 19 278.4 and 202 19 279.2 or in the PCT applications PCT/EP02/14187, PCT/EP02/14188 or PCT/EP02/14189):

Catalyst Tubes:

material of the catalyst tubes: ferritic steel;
dimensions of the catalyst tubes: length, for example, 3 500 mm;
external diameter, for example, 30 mm;
wall thickness, for example, 2 mm;

number of catalyst tubes in the tube bundle: for example, 30 000, or 28 000, or 32 000, or 34 000; in addition up to 10 thermal tubes (as described in EP-A 873 783 and EP-A 12 70 065) which are charged in the same way as the catalyst tubes (in a spiral manner rotating from the very outside toward the inside), for example of the same length and wall thickness but having an external diameter of, for example, 33.4 mm and a centered thermowell of external diameter, for example, 8 mm and wall thickness of, for example, 1 mm;
reactor (same material as the catalyst tubes):
cylindrical vessel of internal diameter 6 000–8 000 mm;
reactor hoods plated with stainless steel of the type 1.4541;
 plating thickness: a few mm;
annularly arranged tube bundle, for example with free central space:
diameter of the free central space: for example, 1 000–2 500 mm (for example 1 200 mm, or 1 400 mm, or 1 600 mm, or 1 800 mm, or 2 000 mm, or 2 200 mm, or 2 400 mm);
normally homogeneous catalyst tube pitch in the tube bundle (6 equidistant adjacent tubes per catalyst tube), arrangement in an equilateral triangle, catalyst tube pitch (separation of the central internal axes of immediately adjacent catalyst tubes): 35–45 mm, for example 36 mm, or 38 mm, or 40 mm, or 42 mm, or 44 mm;
the catalyst tubes are secured and sealed by their ends in catalyst tube plates (upper plate and lower plate each having a thickness, for example, of 100–200 mm) and open at their upper ends into a hood joined to the vessel which has an inlet for the starting reaction gas mixture; a separating plate of thickness 20–100 mm disposed, for example, at half the catalyst tube length, divides the reactor space symmetrically into two temperature zones A (upper zone) and B (lower zone); each temperature zone is divided into 2 equidistant longitudinal sections by deflecting plates;
the deflecting plate preferably has annular geometry; the catalyst tubes are advantageously secured and sealed at the separating plate; they are not secured and sealed at the deflecting plates, so that the transverse flow rate of the salt melt within one zone is very constant;
each zone is provided with salt melt as a heat carrier by its own salt pump; the feed of the salt melt is, for example, below the deflecting plate and the withdrawal is, for example, above the deflecting plate;

a substream is, for example, removed from both salt melt circuits and cooled, for example, in one common or two separate indirect heat exchangers (steam generation);

in the first case, the cooled salt melt stream is divided, combined with the particular residual stream and pressurized into the reactor by the particular pump into the appropriate annular channel which divides the salt melt over the circumference of the vessel;

the salt melt reaches the tube bundle through the window disposed in the reactor jacket; the flow is, for example, in a radial direction to the tube bundle;

in each zone, the salt melt flows around the catalyst tubes as dictated by the deflection plate, for example in the sequence from the outside inward, from the inside outward;

the salt melt flows through a window mounted around the circumference of the vessel and collects at the end of each zone in an annular channel disposed around the reactor jacket, in order to be pumped in a circuit including substream cooling;

the salt melt is conducted from bottom to top through each temperature zone.

The reaction gas mixture leaves the reactor of the reaction stage according to the invention at a temperature a few degrees higher than the salt bath entrance temperature. For further processing in a downstream acrolein oxidation stage, the reaction gas mixture is advantageously cooled to from 220° C. to 280° C., preferably from 240° C. to 260° C., in a separate aftercooler which is connected downstream of the reactor of the first stage.

The aftercooler is generally flanged on below the lower tube plate and normally consists of tubes of ferritic steel. Stainless steel sheet metal spirals which may be partly or fully wound are advantageously introduced into the interior of the tubes of the aftercooler, in order to improve the heat transfer.

Salt Melt:

The salt melt used may be a mixture of 53% by weight of potassium nitrate, 40% by weight of sodium nitrite and 7% by weight of sodium nitrate; both temperature zones and the aftercooler advantageously use a salt melt of the same composition; the amount of salt pumped by circulation in the temperature zones may be approx. 10 000 m³/h per zone.

Flow Control:

The starting reaction gas mixture advantageously flows from top to bottom through the first stage reactor, while the salt melts having different temperatures of the individual zones are advantageously conveyed from bottom to top;

Catalyst tube and thermal tube charge (from top to bottom), for example:

Section 1: length 50 cm
steatite rings of geometry 7 mm × 7 mm × 4 mm (external diameter × length × internal diameter) as a preliminary bed.
Section 2: length 140 cm
catalyst charge of a homogeneous mixture of 30% by weight of steatite rings of geometry 5 mm × 3 mm × 2 mm (external diameter × length × internal diameter) and 70% by weight of unsupported catalyst from section 3.
Section 3: length 160 cm
catalyst charge of annular (5 mm × 3 mm × 2 mm = external diameter × length × internal diameter) unsupported catalyst according to example 1 of DE-A 10046957 (stoichiometry: $[Bi_2W_2O_9 \times 2\ WO_3]_{0.5}$ $[Mo_{12}Co_{5.5}Fe_{2.94}Si_{1.59}K_{0.08}O_x]_1$).

In the abovementioned charge, the unsupported catalyst from example 1 of DE-A 10046957 can also be replaced by:

a) a catalyst according to example 1c of EP-A 15565 or a catalyst to be prepared in accordance with this example, except having the active composition $Mo_{12}Ni_{6.5}Zn_2Fe_2Bi_1P_{0.0065}K_{0.06}O_x \cdot 10\ SiO_2$;

b) example No. 3 of DE-A 19855913 as an unsupported hollow cylinder catalyst of geometry 5 mm×3 mm×2 mm or 5 mm×2 mm×2 mm;

c) unsupported multimetal oxide II catalyst according to example 1 of DE-A 19746210;

d) one of the coated catalysts 1, 2 and 3 of DE-A 10063162, except applied in the same coating thickness to support rings of geometry 5 mm×3 mm×1.5 mm 7 mm×3 mm×1.5 mm.

According to the invention, the fixed catalyst bed is advantageously otherwise selected in such a way (for example by dilution with, for example, inert material) that the temperature difference between the heating point maximum of the reaction gas mixture in the individual temperature zones and the particular temperature of the temperature zone generally does not exceed 80° C. This temperature difference is usually ≦70° C., frequently from 20 to 70° C., and this temperature difference is preferably small. For safety reasons, the fixed catalyst bed is also selected in a manner known per se to those skilled in the art (for example by dilution with, for example, inert material) in such a way that the peak-to-salt-temperature sensitivity as defined in EP-A 1106598 is ≦9° C., or ≦7° C., or ≦5° C., or ≦3° C.

EXAMPLES

A reaction tube (V2A steel; external diameter 30 mm, wall thickness 2 mm, internal diameter 26 mm, length: 350 cm, and also a thermal tube (external diameter 4 mm) centered in the middle of the reaction tube to receive a thermal element which can be used to determine the temperature in the reaction tube over its entire length) is charged from top to bottom as follows:

Section 1: length 50 cm
steatite rings of geometry 7 mm × 7 mm × 4 mm (external diameter × length × internal diameter) as a preliminary bed.
Section 2: length 140 cm
catalyst charge of a homogeneous mixture of 30% by weight of steatite rings of geometry 5 mm × 3 mm × 2 mm (external diameter × length × internal diameter) and 70% by weight of unsupported catalyst from section 3.
Section 3: length 160 cm
catalyst charge of annular (5 mm × 3 mm × 2 mm = external diameter × length × internal diameter) unsupported catalyst according to example 1 of DE-A 10046957 (stoichiometry: $[Bi_2W_2O_9 \times 2\ WO_3]_{0.5}$ $[Mo_{12}Co_{5.5}Fe_{2.94}Si_{1.59}K_{0.08}O_x]_1$).

The first 175 cm from top to bottom are thermostatted by means of a salt bath A pumped in countercurrent. The second 175 cm are thermostatted by means of a salt bath B pumped in countercurrent.

The above-described first reaction stage is continuously charged with a starting reaction gas mixture 1 of the following composition, and the loading and the thermostatting of the first reaction tube are varied:

from 6 to 6.5% by volume of propene, from 3 to 3.5% by volume of $H_2O$, from 0.3 to 0.5% by volume of CO, from 0.8 to 1.2% by volume of $CO_2$, from 0.01 to 0.04% by volume of acrolein,
from 10.4 to 10.7% by volume of O$_2$ and
the remainder ad 100% of molecular nitrogen.

The reaction gas mixture flows through the catalyst tube from top to bottom.

The pressure at the entrance to the reaction tube varies between 2.3 and 3.1 bar as a function of the propene hourly space velocity selected.

At the exit of the reaction tube, a small sample is withdrawn from the product gas mixture for gas chromatography analysis. At the end of the temperature zone there is like-wise an analysis point.

The results as a function of catalyst velocities and salt bath temperatures are shown by the following table 1 (the letter E in brackets means example).

TABLE 1 b) Results

| Propene hourly space velocity (l (STP)/ l · h) | $T_A$ | $T_B$ | $T^{maxA}$ | $T^{maxB}$ | $C^P_A$ | $C^P_B$ | $S^{AC}$ | $S^{AA}$ |
|---|---|---|---|---|---|---|---|---|
| 130 (E) | 319 | 319 | 384 | 351 | 66.7 | 95.1 | 92.6 | 5.1 |
| 130 (E) | 327 | 313 | 400 | 330 | 70.3 | 94.8 | 93.9 | 4.4 |
| 185 (E) | 322 | 336 | 380 | 368 | 64.5 | 94.9 | 90.6 | 7.4 |

$T_A$, $T_B$ are the temperatures of the salt baths circulated by pumping in the temperature zones A and B.
$C^P_A$ is the propene conversion at the end of temperature zone A in mol %.
$C^P_B$ is the propene conversion at the end of temperature zone B in mol %.
$S^{AC}$ is the selectivity of acrolein formation in the product gas mixture based on converted propene in mol %.
$S^{AA}$ is the selectivity of acrylic acid by-production in the product gas mixture, based on converted propene in mol %.
$T^{maxA}$, $T^{maxB}$ are each the highest temperature of the reaction gas mixture within the reaction zones A and B in °C.

Comparative Examples

Everything is carried out as in the examples. However, the length of the charging sections of the fixed bed catalyst charges are changed as follows:

Section 2: 125 cm instead of 140 cm.

Section 3: 175 cm instead of 160 cm.

The results are shown by table 2. (C) means comparative example.

TABLE 2

| Propene hourly space velocity (l (STP)/ l · h) | $T_A$ | $T_B$ | $T^{maxA}$ | $T^{maxB}$ | $C^P_A$ | $C^P_B$ | $S^{AC}$ | $S^{AA}$ |
|---|---|---|---|---|---|---|---|---|
| 130 (C) | 319 | 315 | 384 | 360 | 66.4 | 94.9 | 91.8 | 5.6 |
| 130 (C) | 327 | 310 | 400 | 339 | 70.2 | 95.0 | 93.2 | 4.8 |
| 185 (C) | 322 | 331 | 380 | 377 | 64.7 | 94.8 | 89.9 | 7.8 |

Compared to the results in table 1, lower $S^{AC}$ are achieved with comparable $C^P_B$ values.

We claim:

1. A process for partially oxidizing propene to acrylic acid in the gas phase under heterogeneous catalysis by conducting a starting reaction gas mixture comprising propene, molecular oxygen and at least one inert gas, and containing the molecular oxygen and the propene in a molar O$_2$:C$_3$H$_6$ ratio of $\geq 1$, in a reaction stage over a fixed catalyst bed whose active composition is at least one multimetal oxide comprising the elements Mo, Fe and Bi, in such a way that
the fixed catalyst bed is arranged in two spatially successive temperature zones A, B,
both the temperature of temperature zone A and the temperature of temperature zone B are a temperature in the range from 290 to 380° C.,
the fixed catalyst bed consists of at least two spatially successive fixed catalyst bed zones, and the volume-specific activity within one fixed catalyst bed zone is substantially constant and increases sharply in the flow direction of the reaction gas mixture at the transition from one fixed catalyst bed zone to another fixed catalyst bed zone,
the temperature zone A extends up to a conversion of the propene of from 40 to 80 mol %,
on single pass of the starting reaction gas mixture through the entire fixed catalyst bed, the propene conversion is $\geq 90$ mol % and the selectivity of acrolein formation based on converted propene is $\geq 90$ mol %,
the sequence in time in which the reaction gas mixture flows through the temperature zones A, B corresponds to the alphabetic sequence of the temperature zones,
the hourly space velocity of the propene contained in the starting reaction gas mixture on the fixed catalyst bed is $\geq 90$ l (STP) of propene/l of fixed bed catalyst·h
the difference $T^{maxA}-T^{maxB}$, formed from the highest temperature $T^{maxA}$ which the reaction gas mixture has within temperature zone A, and the highest temperature $T^{maxB}$ which the reaction gas mixture has within temperature zone B is $\geq 0°$ C.,
wherein the transition from temperature zone A to temperature zone B in the fixed catalyst bed does not coincide with a transition from one fixed catalyst bed zone to another fixed catalyst bed zone.

2. The process as claimed in claim 1, wherein $T^{maxA}-T^{maxB}$ is $\geq 3°$ C. and $\leq 70°$ C.

3. The process as claimed in claim 1, wherein $T^{maxA}-T^{maxB}$ is $\geq 20°$ C. and $\leq 60°$ C.

4. The process as claimed in claim 1, wherein the propene hourly space velocity on the fixed catalyst bed is $\geq 90$ l (STP)/l·h and <160 l (STP)/l·h.

5. The process as claimed in claim 1, wherein the propene hourly space velocity on the fixed catalyst bed is $\geq 160$ l (STP)/l·h and $\leq 300$ l (STP)/l·h.

6. The process as claimed in claim 1, wherein the temperature of reaction zone A is from 305 to 365° C.

7. The process as claimed in claim 1, wherein the temperature of reaction zone A is from 310 to 340° C.

8. The process as claimed in claim 1, wherein temperature zone A extends to a propene conversion of from 50 to 70 mol %.

9. The process as claimed in claim 1, wherein temperature zone A extends to a propene conversion of from 60 to 70 mol %.

10. The process as claimed in claim 1, wherein the O$_2$:propene ratio in the starting reaction gas mixture is from 1 to 2.

11. The process as claimed in claim 1, wherein the chemical composition of the active composition used is unchanged over the entire fixed catalyst bed.

12. The process as claimed in claim 1, wherein the entire fixed catalyst bed comprises not more than 4 fixed catalyst bed zones.

13. The process as claimed in claim 1, wherein, when the active composition is uniform over the entire fixed catalyst bed, the volume-specific active composition in the flow direction of the reaction gas mixture increases by at least 5% by weight at the transition from one fixed catalyst bed zone to another fixed catalyst bed zone.

14. The process as claimed in claim 1, wherein, when the active composition is uniform over the entire fixed catalyst bed, the difference in the volume-specific active composition between the fixed catalyst bed zone having the lowest volume-specific activity and the fixed catalyst bed zone having the highest volume-specific activity is not more than 40% by weight.

15. The process as claimed in claim 1, wherein, when the active composition is uniform over the entire fixed catalyst bed, the difference in the volume-specific active composition between the fixed catalyst bed zone having the lowest volume-specific activity and the fixed catalyst bed zone having the highest volume-specific activity is not more than 40° C. by weight.

16. The process as claimed in claim 1, wherein the last fixed catalyst bed zone in the flow direction of the reaction gas mixture is undiluted and consists only of shaped catalyst bodies.

17. The process as claimed in claim 1, wherein the fixed catalyst bed zone having the highest volume-specific activity does not extend into temperature zone A.

18. The process as claimed in claim 1, wherein there is no transition from one fixed catalyst bed zone to another fixed catalyst bed zone in the fixed catalyst bed within the range of $$X \pm L \cdot \frac{4}{100}$$

where L is the length of the fixed catalyst bed and X is the point within the fixed catalyst bed of transition from temperature zone A to temperature zone B.

* * * * *